United States Patent [19]

Golias et al.

[11] 4,005,434
[45] Jan. 25, 1977

[54] METHOD AND APPARATUS FOR GRAPHIC DENSITOMETER DISPLAY

[75] Inventors: Tipton L. Golias; Gene A. Butts, both of Beaumont, Tex.

[73] Assignee: Helena Laboratories Corporation, Beaumont, Tex.

[22] Filed: Mar. 24, 1975

[21] Appl. No.: 561,618

[52] U.S. Cl. .............................. 346/1; 235/151.35; 346/13; 346/33 A; 346/49; 356/201
[51] Int. Cl.² .......................................... G01D 9/28
[58] Field of Search ............. 346/33 A, 13, 49, 66, 346/65, 1; 356/201, 39, 203; 235/151.35, 151.3, 196

[56] References Cited
UNITED STATES PATENTS

| | | | |
|---|---|---|---|
| 3,706,877 | 12/1972 | Clifford et al. | 235/151.35 |
| 3,750,187 | 7/1973 | Keefer | 346/49 |
| 3,842,422 | 10/1974 | VandenBroek | 346/49 X |
| 3,902,813 | 9/1975 | VandenBroek | 356/201 |

Primary Examiner—Joseph W. Hartary
Attorney, Agent, or Firm—Cullen, Settle, Sloman & Cantor

[57] ABSTRACT

An improved method for graphically displaying optical density patterns generated by a densitometer which scans a sample to generate analog signals indicative of the optical density of the sample. The maximum amplitude and cumulative amplitude of the analog signals are computed and stored simultaneously as normalizing signals. The sample is again scanned to recreate the analog signals which are directed in two paths toward two graphic display units. The recreated analog signals directed toward the first display unit are modified by the normalizing amplitude signal to create a visual display curve of the normalized density. The recreated analog signals directed toward the second display unit are modified by the normalizing cumulative amplitude signal to create a visual display of the normalized area under the density curve.

The apparatus includes a scanning system having circuitry to provide analog signals indicative of the optical density of the sample and a pair of conventional graphic display devices. The analog signals are generated during a first scan of the sample and the maximum value is measured and stored in a digital-to-analog converter circuit while the cumulative value is simultaneously measured and stored in a voltage controlled digital-to-analog converter circuit. Each stored value is referred to as a normalizing signal. The sample is again scanned to regenerate the analog signals which are fed along two paths, one to drive each display device. The regenerated analog signals are modified along the two paths by each normalizing signal, respectively, and a modified signal drives each display device to provide visual displays of the normalized optical density curve and the normalized area under the optical density curve, respectively.

14 Claims, 7 Drawing Figures

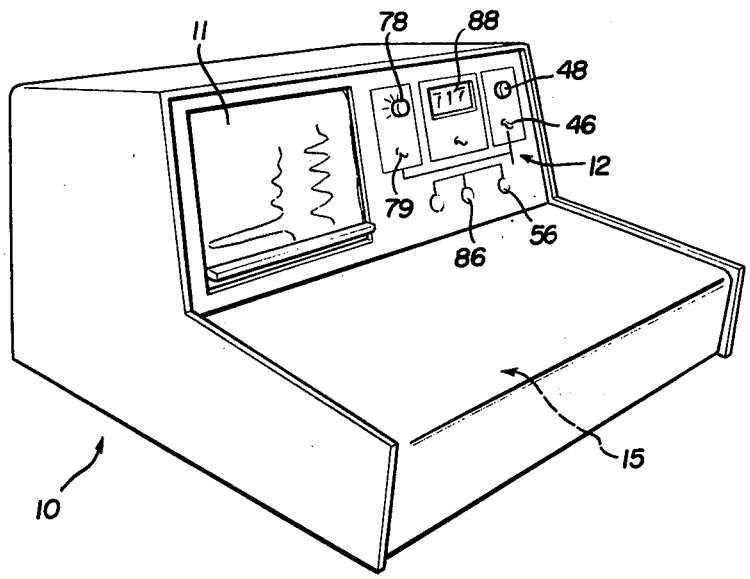
FIG. 1
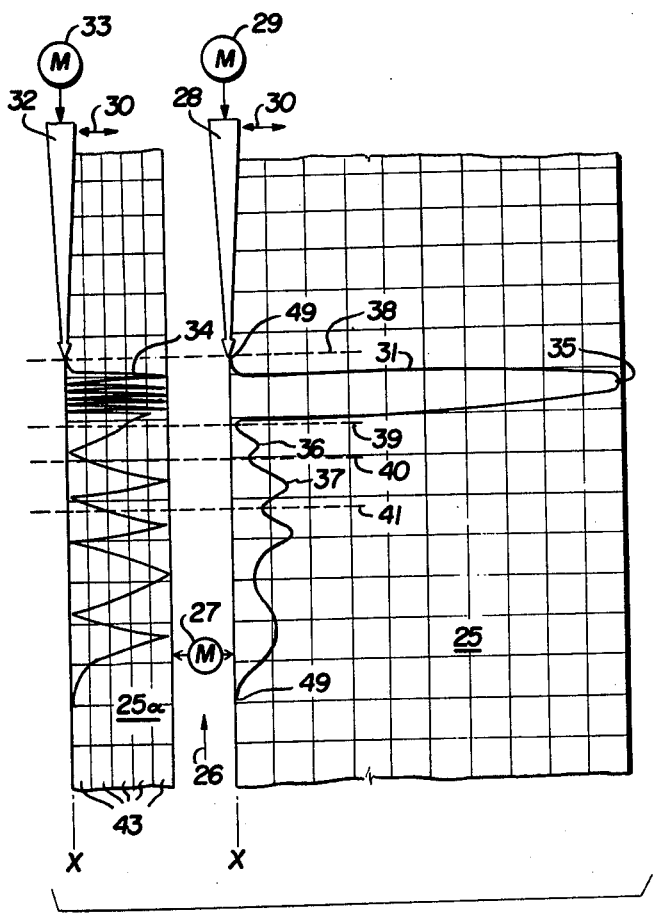
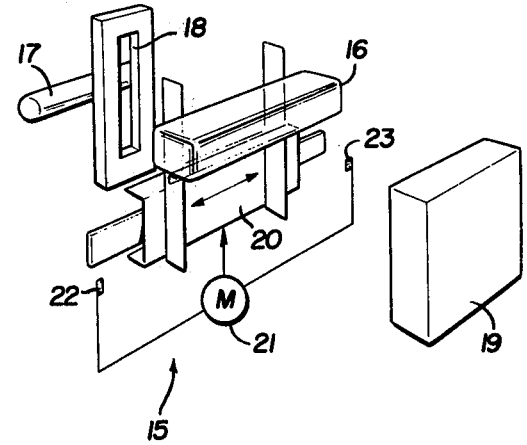
FIG. 2
FIG. 3

METHOD AND APPARATUS FOR GRAPHIC DENSITOMETER DISPLAY

BACKGROUND OF THE INVENTION

This invention relates in general to densitometers and, more particularly, to an improved method and apparatus for graphically displaying densitometer output. Densitometers are, of course, well known as devices which scan a sample and provide an output signal or graphical display indicative of the optical density of the scanned sample.

One well known use of the densitometer is to scan a sample of blood which has been prepared by the electrophoresis process. Electrophoresis of blood samples isolates various proteins in the blood, known as albumin, alpha-1 globulin, alpha-2 globulin, beta-globulin and gamma-globulin. The electrophoresis technique separates these proteins from each other and then the sample may be processed or scanned in a densitometer. Each of the proteins exhibits a different light absorption characteristic or pattern and the light absorption patterns are graphically displayed by the densitometer to indicate the presence and quantity of each protein.

In optical density analysis, the amount of light passing through the sample is an inverse logarithmic function of the optical density of the sample. Thus, if the optical density of the sample is doubled the transmitted light is reduced by a factor of ten. The light transmitted through the sample falls on a photo-responsive element which generates electrical signals having a current proportional to the amount of transmitted light. The current output of the photo-responsive element is, therefore, also a logarithmic function of the optical density which then is converted into analog or time varying signals directly proportional to the optical density pattern of the scanned sample. The analog signals drive a graphic display unit to provide a permanent curve or record of the optical density pattern. All this is well known.

The analog signals, when graphically displayed, exhibit a series of peaks and valleys. In the analysis of blood, the area under the optical density curve and bounded by the two adjacent valleys separated by one peak, is representative of the quantity of each protein in the sample. The important data is the relative percentage of each protein, and the selection of these boundaries, i.e., the precise locations of these valleys, is arbitrary and hence is the basic problem since errors will result in inaccurate analysis of the sample. The problem in not unique to evaluation of blood samples but is common to optical and magnetic density evaluations and, in fact, to all evaluations of analog data.

There are various prior art systems which have considered this problem and which provide a standardized graphical display of the densitometer output. For example, U.S. Pat. No. 3,706,877 issued Dec. 19, 1972 to George F. Clifford, Jr., et al, and U.S. Pat. No. 3,784,789 issued Jan. 8, 1974 to Vanden Brock, each disclose a system for analyzing the densitometer output. The densitometer output is graphically displayed as an analog signal or curve indicative of optical density and a second signal which is the integral of the optical density, i.e., the area under the optical density curve, and which may be either analog or numerical, or both.

There are three common techniques for determining the location of these boundaries or valleys. In a first technique, the densitometer includes circuitry to automatically detect the valleys between the peaks based upon changes in the slope of the curve, integrate the area under the curve between valleys and print out the integral in numerical form. Then, in order to determine the percent of each protein, the operator of the equipment has to add the printed values to obtain a denominator and then calculate each percent by dividing each printed value by the calculated denominator.

Not only is this time consuming but if, in fact, the computer system erroneously selected a particular boundary location, the results are useless to the physician evaluating the blood sample. Hence, the results of a computer print-out cannot conveniently be utilized for subsequent evaluation if the physcian analyzing the blood sample disagrees with the particular boundaries selected by the computer.

The second type of system provides two graphic displays, the first being the optical density of the scanned sample and the second being the integral of the optical density pattern. These are plotted or traced on graph paper and at a later time, the physician can select the particular boundaries for each protein. Then the area under the curve is calculated by actually manually counting the number of squares under the curve between each pair of boundaries which is equivalent to the aforementioned printed values. Again the percentage of each protein is then calculated by the addition and division procedure explained previously. Again, however, this requires laborious manual counting as well as manual calculations.

Finally, the third type of system provides both of these techniques together, i.e., a numerical print-out and a curve, so that the boundaries may be manually selected if the physician is not satisfied with the automatically selected boundaries. However, this still does not eliminate the manual counting and addition-division procedure for obtaining percentages of each protein.

BRIEF DESCRIPTION OF THE INVENTION

We have discovered that at least part of the problem in determining location of boundaries or valleys may be attributed to the failure of the graphic display to utilize a maximum amount of space on the graph paper. Specifically, we have discovered that maximum utilization of the graph paper reduces the error in selecting boundaries. To obtain such maximum utilization of the optical density curve, we have discovered that it is advantageous to initially determine the maximum optical density of the particular samples during a first scan and to display this value as unity while graphically displaying the optical density pattern during the second scan. Setting this maximum optical density to unity is called mathematically normalizing the graphic display. This normalizing technique expands the graphic display without distortion and thus provides more pronounced valleys or boundaries.

In addition, we have determined that by providing a curve which is the normalized integral of the optical density pattern, when the technician or physician satisfies himself as to the location of each boundary for each protein, then the process of determining the percentages for each protein no longer requires the aforementioned addition-division steps but may be evaluated directly.

Thus, the present invention is directed to a method and apparatus for providing normalized graphic displays of the optical density pattern and area under the optical density pattern so that the boundaries may be more accurately selected and so that the quantity and percent of each protein may be directly evaluated at any time. This provides a great benefit when it is desired to change the location of arbitrarily selected boundaries during subsequent evaluation of the graphic display.

OBJECTS OF THE INVENTION

It is, therefore, an object of the present invention to provide an improved method for graphically displaying the output of a densitometer by providing a normalized display of the optical density curve and by providing a normalized display of the area under the optical density curve.

It is an object of the present invention to provide an improved apparatus for graphically displaying the optical density pattern of a sample including generating analog signals representative of the optical density, generating the integral of the analog signals, normalizing the analog signals, normalizing the intergral of the analog signals, and graphically displaying both the normalized analog signals and the normalized integral of the analog signals.

It is yet another object of the present invention to provide an improved method for graphically displaying optical density patterns including scanning the sample, generating a time varying signal representative of the optical density of the sample and driving two displays with the time varying signal and further including storing the maximum optical density signal and the cumulative optical density signal, and modifying the time varying signal to each display, so that the first display provides the normalized optical density curve and the second display provides the normalized area under the optical density curve.

It is yet a further object of the present invention to provide an improved apparatus for graphically displaying optical density patterns of blood samples or the like including a scanning means for relatively moving the sample, a light source, and a photo-responsive element; a circuit for converting the output of the photo-responsive element into analog signals; a pair of graphic displays each driven by the analog signals to provide a first display curve of the optical density pattern and a second display of the area under the optical density curve, circuit means for calculating and storing the maximum analog signals and for normalizing the analog signals, to provide a normalized optical density display curve, and circuit means for calculating and storing the cumulative analog signals and for normalizing the cumulative analog signals to provide a normalized display of the area under the optical density curve.

Still another object of the present invention is the provision of an improved method for graphically displaying optical density patterns including scanning a sample in a first direction to generate analog signals, storing the maximum and cumulative values of the analog signals, respectively, scanning the sample in a second direction to recreate the analog signals, and driving a pair of display units with said recreated analog signals, with each display unit having its driving signals modified by one of said stored signals to provide a normalized optical density display and a normalized cumulative optical density display.

IN THE DRAWINGS

The various objects of the present invention, together with other objects and advantages which may be attained by its use, will become more apparent upon reading the following detailed description taken in conjunction with the drawings.

In the drawings, wherein like reference numerals identify corresponding parts:

FIG. 1 is a perspective illustration of the densitometer of the present invention.

FIG. 2 is a diagramatic illustration of the scanning system of the present invention.

FIG. 3 is an illustration of typical graphic displays generated according to the principles of the present invention.

AS SHOWN IN THE DRAWINGS

Figure 4:
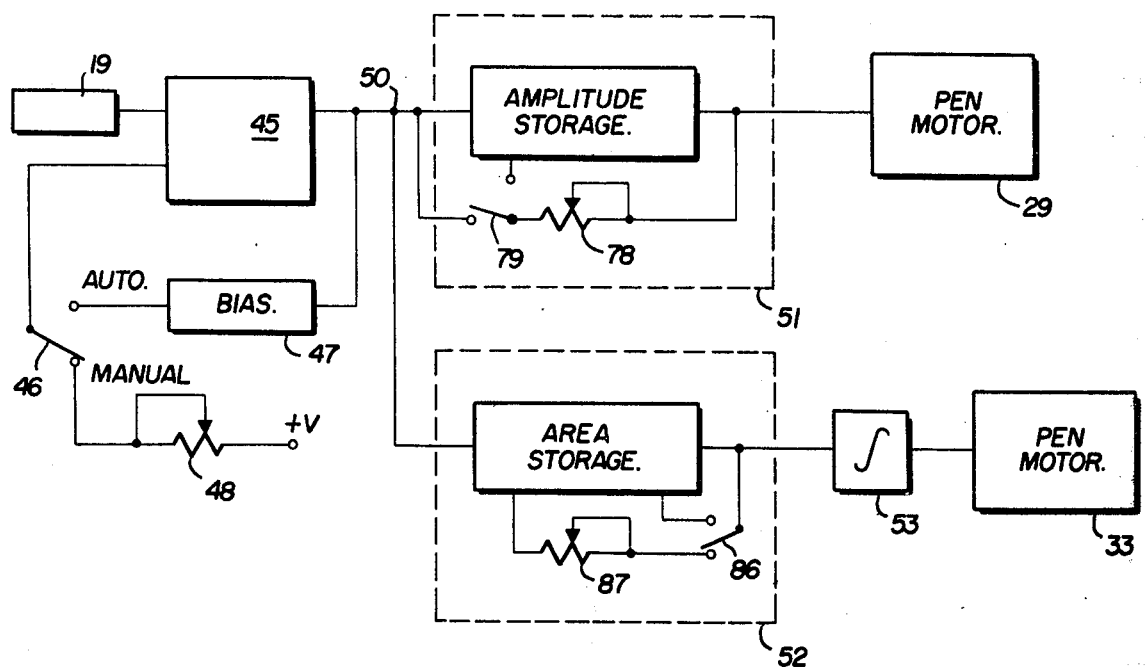
FIG. 4 is a block diagram illustrating the method and apparatus of the present invention.

With reference to the drawings, there is illustrated a densitometer 10 operable in accordance with the principles of the present invention including a display area 11 and a control panel 12 which will be explained in greater detail hereinafter. The densitometer includes a scanning means generally designated as 15 for generating optical density signals of a sample 16 which has been prepared by the electrophoresis technique. The scanning means broadly includes a light source 17, which may be fluorescent or incandescent depending upon the type of sample utilized, which emits light through a slit 18 onto the sample. The light transmitted through the sample, i.e., that light which is not absorbed by the sample, is detected by a photo-responsive element 19 and the current generated by the photo-responsive element is proportional to the amount of light transmitted through the sample. Thus, the sample 16 is scanned through an optical path defined by the light source 17, slit 18, and photo-responsive element 19, as is well-known.

The scanning, however, is accomplished in a unique manner with the sample 16 held in a movable carriage 20 which is moved or scanned through the optical path by a reversible motor 21. A pair of limit switches 22, 23 serve to both limit the extent of travel of the carriage in each direction and also to reverse the motor.

As is conventional, the output of the photo-responsive device 19 is ultimately displayed on a cross-hatched or graph paper 25, 25a, which is advanced in the direction of arrow 26 by a motor 27. A first pen 28 driven by a motor 29 provides a trace or analog display of this output which, in a preferred embodiment, is the optical density of the sample. The paper 25 moves longitudinally in the direction of arrow 26 and the pen 28 reciprocates longitudinally in the direction of arrow 30 and the combination of movement provides the curve illustrated as 31.

A second pen 32 driven by a second motor 33 provides a curve 34 which is the integral or area under the curve 31. Pen 32 also reciprocates longitudinally in the direction of arrows 30.

In order to better understand the principles of the present invention, curve 31 has been marked to indicate a first peak 35 which is representative of the albumin in the blood sample and second and third peaks 36 and 37 indicative of alpha-1 and alpha-2 globulin, respectively. Horizontal dashed lines 38, 39, 40 and 41, serve as boundary lines for each of these proteins and are drawn by the operator of the apparatus after the curves have been drawn by the pens.

The unique benefit of the normalization technique may now be appreciated. The portion 25a of the graph paper has a series of vertical grid lines defining 5 spaces 43 therebetween. The number of space 43 (or grid lines) traversed by curve 34 is proportional to the area under curve 31. Thus, when curve 34 is normalized according to the present invention, each space 43 crossed by the curve is equal to one percent of protein.

Consider protein alpha-1 having a peak 36 (curve 31) and defined between valleys or boundaries 39, 40. Curve 34, between those boundaries, crosses 4 space 43. Hence, there is four percent of alpha-1 in the sample. Similarly, alpha-2, peak 37 bounded by valleys 40, 41, crosses 10 ½ spaces, hence there is 10.5 percent of alpha-2 in the sample.

From the foregoing it may be seen that the addition-division problem of the prior art has been eliminated. Furthermore, should the physician decide that boundary lines 38–41 have been incorrectly selected, then they are merely redrawn and the crossings of spaces 43 by curve 34 recounted to provide a direct reading of the percent of each protein in the sample.

With reference now to FIG. 4, a block diagram of the circuit for providing this result will now be explained. A photo-responsive device 19 generates a current proportional to the light transmitted through the sample 16 which is coupled through a logarithmic converter 45 and inverter 55, which may include a TD 401 transistor serving as the logarithmic converter and an operational amplifier such as a 741 having its positive input grounded serving as the inverter. The use of the TD 401 transistor as a logarithmic converter is conventional since it is known that the base-to-emitter voltage of a transistor is equal to the "log" of the collector current. In order to prevent the curves 31 and 34 from drifting above their "X" axes, a biasing or zeroing network is provided for the logarithmic converter 45. In a preferred embodiment the biasing is automatic although the present invention includes the option of a manual biasing network.

To accomplish the bias function, the output of the logarithmic converter 45 is coupled through a first switch 46 (which is also shown as part of the control panel 12 of FIG. 1) to an automatic biasing or zero circuit 47 or a manual biasing network including a potentiometer 48. As illustrated in FIG. 3, the effect of automatic zeroing is shown at two regions 49 of curve 31 where the curve is shown on the X axis of the graph indicating the absence of drift or bias. Biasing also compensates for aging of the circuit components.

The output of the converter and inverter 45, 55, in an analog signal at terminal 50. The analog or time varying signals, which are representative of the changing optical density during scanning, serves as the input to an amplitude control circuit 51 and an area control circuit 52. The output of the amplitude control circuit 51 controls the pen motor 29 of the pen 28 to provide the curve indicative of the optical density of the scanned sample. The output of the area control circuit 52 is coupled through a dual slope integrator 53 to the motor 33 of the pen 32. The function of the dual slope integrator 53 is to provide the curve 34 which is the integral of the area under the curve 31 and which oscillates or travels back and forth between upper and lower limits thus providing a cumulative folded integral signal as is well known.

Figure 5:
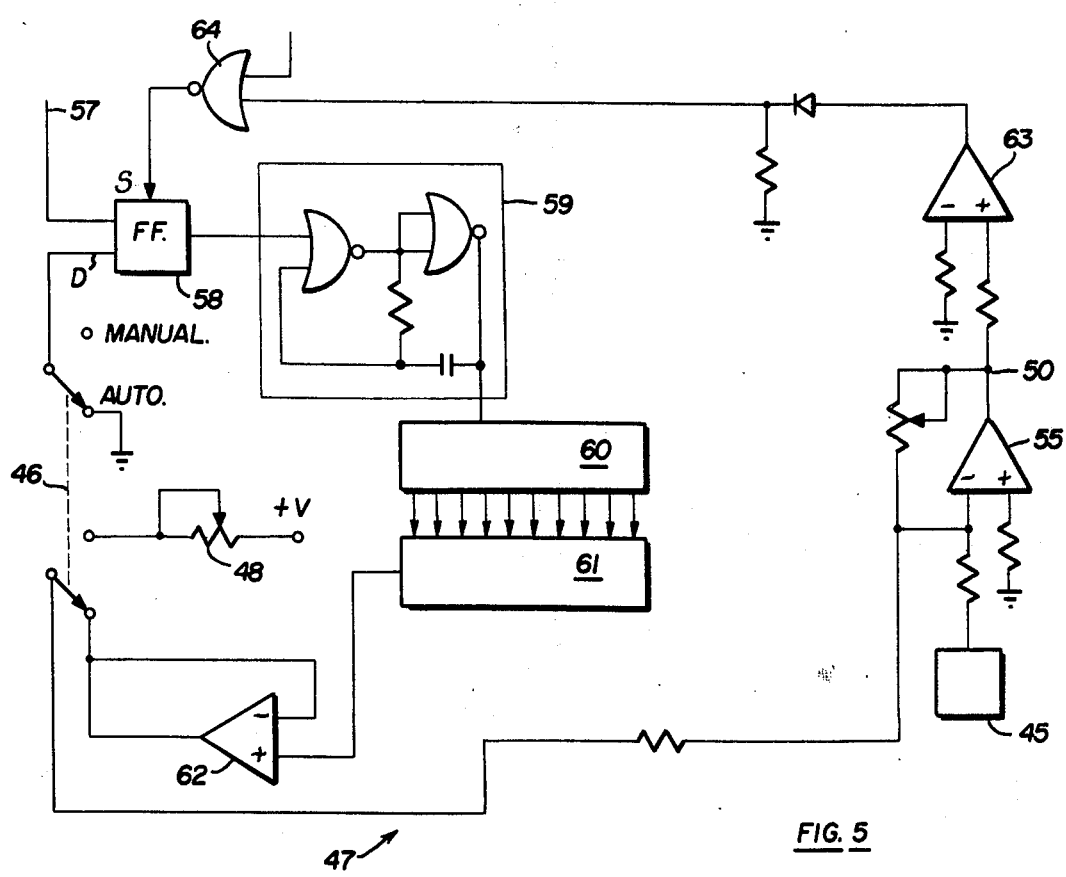
FIGS. 5–7 are schematic circuit diagrams illustrating various features of the present invention in greater detail.

With reference to FIG. 5, the automatic zeroing or biasing network 47 is illustrated in conjunction with the logarithmic converter 45 the output of which is coupled through an inverter 55 to the terminal 50. It is the output of the inverter, i.e., the signal at the terminal 50, which must be automatically adjusted to zero. This is accomplished automatically before the start of the scanning, as follows. The operator depresses a scan control 56 on the control panel 12 which provides a signal on line 57 to the C terminal of flip flop 58. The output of the flip flop is low and drives a 1 KC oscillator 59. The digital or pulse output of the oscillator is connected to a digital-to-analog converter including a 12 bit binary counter 60, such as an RCA CD 4040 having its twelve parallel outputs connected to an R2R binary ladder 61 such as an HC 210-LD. The output of the ladder is an analog signal which is coupled to a differential amplifier 62 operating as a buffer to avoid impedance loading of the ladder. The output of the ladder is an analog signal which increases in magnitude during the time the oscillator 59 is on. Thus, there is a digitally generated ramp signal applied to the differential amplifier or buffer 62. The output of the buffer 62 runs through switch 46 to one input of the gain amplifier 55 providing a biasing signal to compensate for the signal from the logarithmic converter 45 and the gain amplifier itself.

The output of the gain amplifier 55 at terminal 50 is fed back through a comparator 63. When the two inputs to the comparator are equal, indicating a zero output at terminal 50, the comparator goes low and provides a low signal to the NOR gate 64. The other input to the NOR gate 64 is low only when carriage 20 contacts limit switch 22. At all other times this input is high, hence the NOR gate output to the S terminal of the flip flop 58 is high, setting the flip flop high and thus turning off the oscillator 59. This inhibits erroneous rezeroing during the remainder of the scan cycle.

The foregoing explains the unique use of an oscillator operating in a digital mode to activate a counter and generate a ramp signal at the output of the binary ladder which ramp signal provides a bias to the inverter 55. The benefit of this circuit is that the bias is not provided across a capacitor which may discharge during scanning. The bias being digitally generated remains as an input to the inverter until the apparatus is turned off.

If the operator of the machine wishes to manually adjust the gain in lieu of the automatic bias or zeroing system described, switch 46 is moved to the manual position and the potentiometer 48 on the control panel is adjusted by the operator to provide the desired zeroing. It is noted with respect to FIG. 5 that by moving switch 46 to the manual position, the input at the D terminal of the flip flop 58 is removed thus preventing the flip flop from being cleared and thus preventing the oscillator 59 from being turned on.

In the operation of the densitometer of the present invention, the complete scan cycle of the sample includes scanning in a first direction the full length of the sample and then reversing the carriage 20 by means of reversible motor 21 and scanning the full length of the sample in the opposite direction. To provide this feature, the motor 21 is reversible and limit switches 22 and 23 are provided to limit the length of travel of the carriage 20. As the carriage 20 travels its full distance and hits a limit switch 23, the motor 21 is reversed thereby moving the carriage in an opposite direction until the limit switch 22 is reached at which time the scan cycle is complete. The purpose of this bi-directional scan is as follows. During the first scan the display pens are inactive. Data is being stored and calculated in the amplitude and area control circuitry during this first scan. Specifically, the maximum and cumulative analog signals are both being computed, and stored. During the reverse scan the stored signals are used to modify the new analog signals to drive the pens and provide normalized displays.

Figure 6:
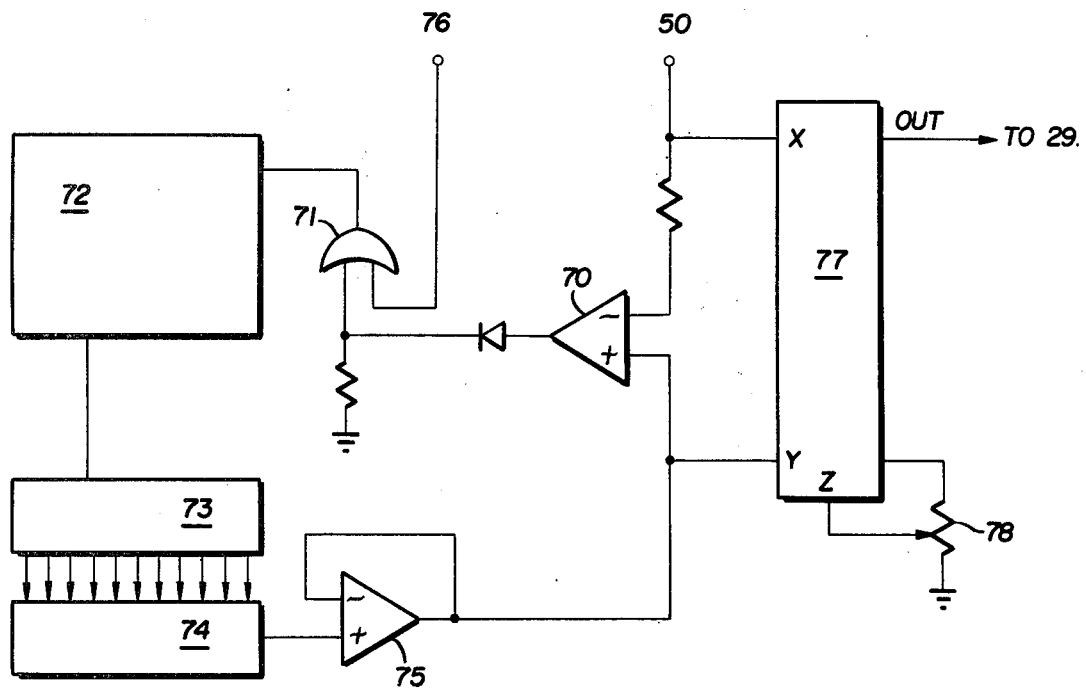

Referring to FIG. 6, the circuitry for storing the maximum analog or optical density signals will now be explained. This amplitude control or amplitude normalizing circuitry 51 of FIG. 3, is illustrated as starting with the analog input signals from terminal 50 and utilizing these signals as one input to a comparator 70 which compares the magnitude of the input signals with the magnitude of all prior input signals during that same first scan. The output of the comparator 70 is fed through an OR gate 71 to an oscillator 72. When the oscillator 72 is activated it generates digital pulses to another CD 4040 12 bit binary counter 73 the output of which is coupled along its parallel paths to a R2R HC 210-LD binary ladder 74. Again, to avoid loading the ladder an output buffer 75 is provided to receive the output of the ladder 74. The output of this buffer 75 is coupled to the positive terminal of the peak comparator 70. In operation, this circuit acts as a digital-to-analog convertor, similar to FIG. 5, and provides a digitally generated signal as the output of the buffer 75. By applying the analog input signals at terminal 50 to the negative side of the comparator 70, the comparator provides a negative output each time the analog signal at terminal 50 exceeds the previously stored maximum signal. This negative or low input provides a low output from the OR gate 71 which turns on the oscillator. As the output ramp from the ladder 74 increases through the output buffer 75, a signal is reached at the positive input of the comparator 70 which equals or exceeds the analog input from terminal 50. This drives the comparator 70 positive and the OR gate 71 high, turning off the oscillator.

Hence, the oscillator 72 is "on" only when the analog input signals at terminal 50 are greater than the signal from the peak buffer 75 which, in fact, is the analog output of the ladder 74. At the completion of the first half of the scan, i.e., the completion of scanning in the first direction, the output of the ladder 74, and hence, the output of buffer 75, reflects the maximum analog optical density signal obtained during the scan. Completion of the first scan trips limit switch 23 which not only causes the carriage motor 21 to be reversed but provides a signal at terminal 76 providing a high signal OR gate 71 thereby turning off the oscillator for the duration of the bi-directional scan cycle.

During the second half of the scan, i.e., the reverse direction of scanning, the analog signals at terminal 50 indicative of the optical density then being scanned appear as the X input to a ratio module 77 which may be an Intech A-734. The maximum analog signal stored in the buffer 75 appears as the "Y" input to the module 77. The output of the ratio module 77 is the ratio of the analog input signals at terminal 50 to the most dense or maximum input from peak buffer 75 at terminal Y. This provides a normalized amplitude signal, i.e., an amplitude signal which is unity at one point during the output curve and otherwise lower than unity.

Explaining the operation of the circuit of FIG. 6 in concise terms, the circuit operates as a digital peak follower producing analog signal outputs proportional to the binary count which was generated by oscillator pulses. The oscillator is turned on only when the analog input signals are higher than the highest analog signal previously occurring during the scan. The benefit of the digital peak follower system is to avoid drift and to avoid the problems inherent in utilizing a capacitor to store a maximum signal, i.e., premature discharge of a capacitor. The output of the peak buffer 75 is maintained during the entire scan cycle.

The benefit of amplitude normalization is to provide a maximum deflection of the pen at one point of the output curve, that point being equal to the darkest or most dense portion of the sample. Displaying the curve to its fullest extent presents the most definitive display of optical density thus permitting the boundaries between protein peaks to be more accurately determined by inspection of the curve.

If it is desired to set the maximum optical density to a value less than one, this feature is provided by the amplitude normalization circuit of the present invention. Specifically, the ratio module 77 includes a manual gain adjust in a form of a potentiometer 78 coupled to the "Z" input of the ratio module. This potentiometer is also illustrated in FIG. 4 as part of the amplitude normalizing circuit 61. When the potentiometer 78 is utilized, this reduces the output of the ratio module 77 to any desired percent or fraction of unity. Similarly, by-pass switch 79 permits the use of only potentiometer 78.

Figure 7:
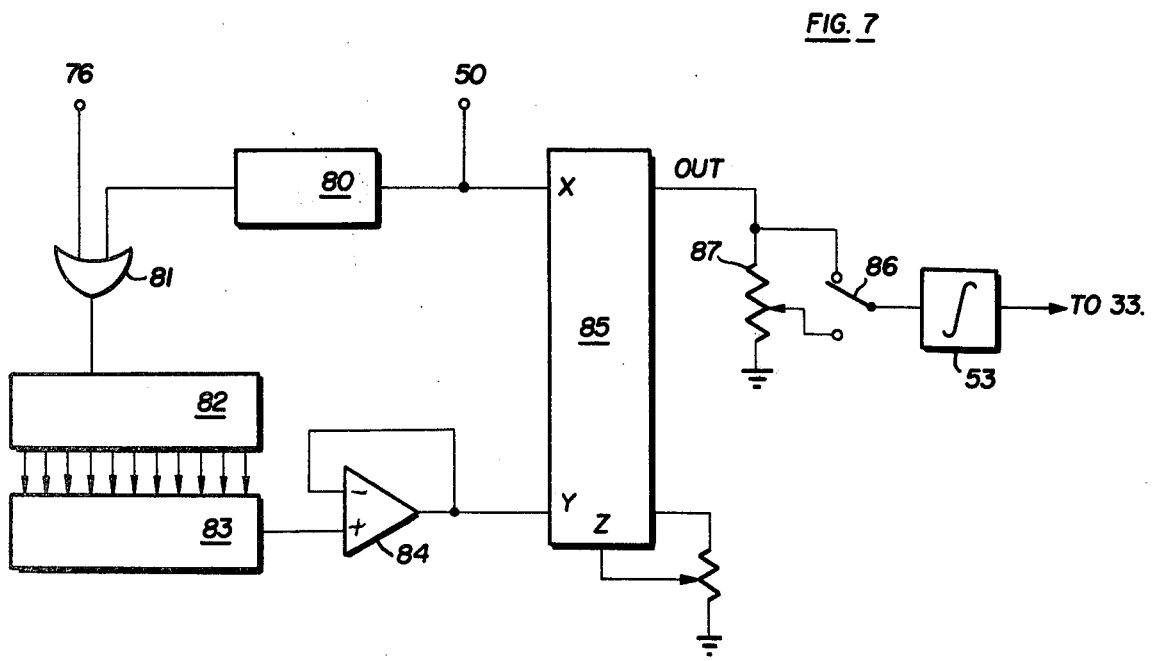

Simultaneously with the amplitude or peak normalization according to the circuit of FIG. 6, the same analog signal at terminal 50 serves as the input to the area normalizing circuit of FIG. 7. The circuit of FIG. 7 operates during the scan in the first direction to store the total area under the analog curve. Then during the reverse direction scan this total area is utilized to provide a normalized area signal.

More specifically, during the scan in the first direction, the analog signals serve as the input to a voltage controlled oscillator 80. The voltage controlled oscillator is a voltage-to-frequency converter such as an Intech 843 and provides output pulses proportional in frequency to the instantaneous voltage of the analog signals at terminal 50. The output pulses of the controlled oscillator 80 serves as one input to an OR gate 81. The output of the OR gate serves as the input to a digital to analog converter including another CD 4040 12 bit binary counter 82 and a R2R binary ladder 83. The output of the ladder is an analog signal indicative of the cumulative magnitude of the analog input signals at terminal 50, i.e., an analog signal equal to the area under the curve of the optical density. This is supplied first to a buffer 84 which is utilized to prevent loading on the output of the ladder 83 and then to a ratio module 85. Again, the use of a digital to analog converter circuitry in lieu of storing the accumulated voltage on a capacitor serves to eliminate the problem of capacitor drain and provides a drift-free voltage signal thereby increasing accuracy. During the first scan when the limit switch 23 is reached, the signal at terminal 76 (the same signal utilized to turn off the oscillator of FIG. 6), prevents the binary ladder from accumulating additional pulse signals. During the second scan, the analog input at terminal 50 is supplied as the X input to the ratio module 85 and the total area under the curve is supplied as the Y input to the ratio module 85. As the analog input at terminal X is varied by the optical density of the sample being scanned, the output of the ratio module 85 provides a ratio of the instaneous voltage of the analog signal to the total area under the curve.

The output of the ratio module 85 may be utilized in one of two fashions and a switch 86 is provided for selection therebetween. When switch 86 is in the upper position as shown in FIG. 7, the output of the ratio module 85 is not modified. Hence, a total area under curve 34 will be normalized. i.e., will equal unity.

Often, values for various protein fractions in the blood are expressed in terms of grams percent of the total protein. Typically, this was done in the past by first obtaining the total protein value for the sample by a wet chemistry or optical method. This value is then multiplied by the relative ratio of each particular protein to the total amount of protein which results in the gram percent value for each protein fraction.

According to the principles of the present invention, a scaling feature is provided whereby the total anticipated protein may be entered as the denominator of a modification scaling factor. Then, the output of the ratio module 85 is modified by this scaling factor so that the area under the curve for each particular protein, i.e., the area between boundaries, provides a direct reading in "grams percent" of protein in lieu of a reading of percentages.

To provide this, the switch 86 is moved to the lower position. The output signal from the log ratio module 85 is directed through a potentiometer device which, in fact, is known as a Kelvin Varley thumb wheel digivider. Numerical values from 000 to 999 representing a decimal of .000 to .999 of the output of the ratio module 85 may be selected. This digivider is illustrated schematically as a potentiometer 87 in the circuit of FIG. 7 and as 88 in FIG. 1.

If the digivider is set to a valve other than 000, then the count of the crossings explained previously with respect to FIG. 3 provides a value in grams-percent, rather than percent, but again without further calculation, such as the addition-division technique.

The output of the ratio module 85 is connected through switch 86 to a dual slope integrator 53. This is an integrator with a narrow null and provides what is referred to as a zig-zag or folded integral recording. This zig-zag or folded integral is produced by automatically reversing the direction of the pen 32 as soon as the pen has traversed a certain predetermined recording width on the paper 25a. Such a dual slope integrator is described in U.S. Pat. No. 3,750,187 to Keefer. The output from the dual slope integrator 53 is coupled to the motor 31 of pen 32.

The foregoing is a description of the structure and circuitry of the present invention. It must be appreciated that many modifications and variations may be made without departing from the spirit and scope of the present invention. For example, instead of bi-directional scanning, it is possible to utilize a computer to store the analog signals generated during a signal scan. During that scan the maximum amplitude nd cumulative amplitude of the analog signals are computed as before. At the completion of the scan, the the stored analog signals then are retrieved from the computer and applied as the input to each ratio module. Hence, the language "recreation" or "generation" of analog signals also refers to retrieving signals from a computer or storage device.

Similarly, the present invention may be modified to provide the option of a fluorescent light source in lieu of an incandescent light source. The choice of light sources is dependent upon the particular material to be scanned or sampled.

Also, the present invention may be used for calculating fractional or partial areas under any analog curve without the time consuming, tedious, addition-division procedure.

The foregoing is a complete description of the preferred embodiment of the present invention. The invention should be limited only by the spirit and scope of the following claims.

What is claimed is:

1. In a method of graphically displaying optical density patterns of a sample of blood or the like for subsequent evaluation, including scanning said sample by relatively moving said sample and a light source and a photo-responsive element, converting the output of said photo-responsive element into analog signals with a converting circuit, and driving two display devices with said analog signals to provide graphical representations of the relative optical density and the cumulative optical desnity of said sample, respectively, the improvement of separately storing the maximum amplitude of said analog signals and the amplitude of said cumulative analog signals, and modifying said analog signals by said stored signals prior to driving said display devices to display a normalized optical density curve and a normalized cumulative optical density curve, respectively, said step of separately storing the maximum amplitude of the analog signals including the steps of comparing the instantaneous amplitude of said analog signals with the maximum prior stored analog signals obtained during said scan and if the instantaneous signal is greater than the prior stored maximum signal, actuating an oscillator and converting the oscillator output into a stored signal having an amplitude equal to the instantaneous analog signal.

2. A method as defined in claim 1 wherein said maximum amplitude signal and said cumulative analog signals are stored during a first scanning of said sample, and said analog signals are recreated during a second scanning of said sample, and said recreated analog signals are modified by said stored signals to drive said display devices.

3. A method as defined in claim 1 and including the further step of adjusting the output of said converting circuit to zero prior to said scanning, said adjusting including generating a sequence of digital pulses with an oscillator, converting said pulses to an analog adjusting signal, comparing said analog signals to the adjusting signal, and continuing the generating of pulses until the output of said converting circuit is zero to provide a drift-free adjusting signal for said circut.

4. The invention as defined in claim 1 wherein the maximum cumulative analog signal is stored by the steps of activating a voltage controlled oscillator to provide voltage to frequency conversion, driving a counter with the output of said oscillator, and accumulating the output of said counter to provide a stored analog signal representative of the accumulated value in said counter.

5. In a method for graphically displaying analog signals for subsequent analysis including generating analog signals and driving a pair of display units with said analog signals, the improvement of separately storing the maximum amplitude of the analog signals and the amplitude of the cumulative analog signals, selecting a first predetermined percentage of the stored maximum analog signal, selecting a second predetermined percentage of the stored cumulative analog signal, modifying the analog signals driving the first display unit by said first percentage of the stored maximum analog signal, and modifying the analog signals driving the second display unit by said second percentage of the stored cumulative analog signal to provide modified displays of the maximum and cumulative analog signals, respectively, said step of separately storing the maximum amplitude of the analog signals including the steps of comparing the instantaneous amlitude of said analog signals with the maximum prior stored analog signals obtained during said scan and if the instantaneous signal is greater than the prior stored maximum signal, actuating an oscillator and converting the oscillator output into a stored signal having an amplitude equal to the instantaneous analog signal.

6. The method as defined in claim 5, wherein said first and second percentages are each 100.

7. In an apparatus for graphically displaying optical denity patterns of a scanned sample of blood of the like including a light source, a photo-responsive element, and means for relatively moving said sample and said light source and said photo-responsive element, a circuit for converting the output of said photo-responsive element into analog signals, and a pair of graphic display devices each driven by said analog signals to provide graphical displays of said analog signals and the cumulative analog signals, respectively, the improvement of: an intermittently operable amplitude responsive circuit for storing the maximum analog signals, a continuously operable amplitude responsive circuit for storing the cumulative analog signals, and a pair of ratio circuits, each for modifying the analog signals with a preselected percentage of one stored signal, respectively, prior to driving said display devices, said intermittently operable circuit including an oscillator for generating pulses, a digital to analog converter for counting and storing said oscillator pulses, and a comparator for comparing the magnitude of the analog signals with the output of the digital-to-analog converter and for actuating said oscillator only while the magnitude of the analog signals exceeds the converter output.

8. The apparatus as defined in claim 7 wherein both of said preselected percentages are 100, to produce normalized graphic displays of said analog signals and said cumulative analog signals, representing the normalized optical density curve and the normalized area under the optical density curve, respectively.

9. The apparatus as defined in claim 7 wherein said sample is scanned twice, the first scan for generating and storing said maximum signals and said second scan for recreating said analog signals to be modified by said stored signals and to drive said display devices.

10. The invention as defined in claim 9 wherein said relative moving means includes a movable carriage to hold said sample, a pair of spaced-apart limit switches to define and limit the extent of travel of said carrige, and a reversible motor responsive to said limit switches to bi-directionally move the carriage, said first and second scans being in opposite longitudinal directions.

11. The apparatus as defined in claim 7 wherein said continuously operable circuit includes an oscillator having output pulses of a frequency proportional to the amplitude of the analog signals, and a digital-to-analog converter for counting and storing the pulses from said oscillator.

12. The invention as defined in claim 7 and further including a biasing network to zero the output of said photo-responsive converting circuit, said biasing network including an oscillator for generating a series of pulses, a digital-to-analog converter responsive to said pulses to provide analog bias signals, and a comparator reponsive to the output of said converter circuit and said digital-to-analog converter for continuing the generation of pulses from said oscillator until the output of said comparator is zero.

13. In an apparatus for graphically displaying optical density patterns of a scanned sample of blood or the like, including a light source, a photo-responsive element, and means for relatively moving said sample and said light source and said photo-responsive element, a circuit for converting the output of said photo-responsive element into analog signals, and a pair of graphic display devices each driven by said analog signals to provide graphical displays of said analog signals and the cumulative analog signals, respectively, the improvement of: an intermittently operable amplitude responsive circuit for storing the maximum analog signals, a continuously operable amplitude responsive circuit for storing the cumulative analog signals, and a pair of ratio circuits each for modifying the analog signals by one of said stored signals, respectively, prior to driving said display devices for displaying a normalized optical density curve and a normalized cumulative optical density curve, respectively, said intermittently operable amplitude responsive circuit including an oscillator for generating pulses, a digital to analog converter for counting and storing said oscillator pulses, and a comparator for comparing the magnitude of the analog signals with the output of the digital to analog converter and for actuating said oscillator only while the magnitude of the analog signals exceeds the converter output, and said continuously operable amplitude responsive circuit including an oscillator having output pulses of a frequency proportional to the amplitude of the analog signals, and a digital to analog converter for counting and storing the pulses from said oscillator.

14. The invention as defined in claim 13 and further including a biasing network to zero the output of said hoto-responsive converting circuit, said biasing network including an oscillator for generating a series of pulses, a digital to analog converter responsive to said pulses to provide analog bias signals, and a comparator responsive to the output of said converter circuit and said digital to analog converter for continuing the generation of pulses from said oscillator until the output of said comparator is zero.

* * * * *